(12) United States Patent
Dennis et al.

(10) Patent No.: US 9,063,161 B2
(45) Date of Patent: Jun. 23, 2015

(54) PORTABLE COAGULATION MONITORING DEVICE FOR ASSESSING COAGULATION RESPONSE

(71) Applicant: Entegrion, Inc., Research Triangle Park, NC (US)

(72) Inventors: Robert Glenn Dennis, Chapel Hill, NC (US); Thomas H. Fischer, Hillsborough, NC (US); Joseph Anthony DaCorta, Chapel Hill, NC (US)

(73) Assignee: Entegrion, Inc., Research Triangle Park, NC (US)

( * ) Notice: Subject to any disclaimer, the term of this patent is extended or adjusted under 35 U.S.C. 154(b) by 0 days.

(21) Appl. No.: 13/897,712

(22) Filed: May 20, 2013

(65) Prior Publication Data

US 2013/0267017 A1   Oct. 10, 2013

Related U.S. Application Data

(62) Division of application No. 12/971,013, filed on Dec. 17, 2010, now Pat. No. 8,450,078.

(60) Provisional application No. 61/287,780, filed on Dec. 18, 2009.

(51) Int. Cl.

| G01N 33/86 | (2006.01) |
| G01N 21/17 | (2006.01) |
| G01N 33/49 | (2006.01) |
| G01N 11/00 | (2006.01) |

(52) U.S. Cl.
CPC ............. *G01N 33/86* (2013.01); *G01N 21/17* (2013.01); *G01N 33/4905* (2013.01); *G01N 2011/008* (2013.01)

(58) Field of Classification Search
CPC ..................................................... G01N 21/17
USPC ....................................................... 435/287.1
See application file for complete search history.

(56) References Cited

U.S. PATENT DOCUMENTS

| 5,181,415 | A | 1/1993 | Esvan et al. |
| 5,838,515 | A | 11/1998 | Mortazavi et al. |
| 6,060,323 | A | 5/2000 | Jina |
| 7,005,857 | B2 | 2/2006 | Stiene et al. |
| 7,074,582 | B2 | 7/2006 | Fischer et al. |
| 7,361,306 | B2 | 4/2008 | Bote |
| 7,399,637 | B2 | 7/2008 | Wright et al. |
| 2004/0175296 | A1 | 9/2004 | Opalsky et al. |
| 2005/0015001 | A1 | 1/2005 | Lec et al. |

OTHER PUBLICATIONS

Hansson et al. "Whole blood coagulation on protein adsorption-resistant PEG and peptide functionalised PEG-coated titanium surfaces", Biomaterials, 2005, 26:861-872.*

Nam et al. "Evaluation of the Roche CoaguChek XS handheld coagulation analyzer in a cardiac outpatient clinic", Annuals of Clinical & Laboratory Science, 38(1):37-40.*

Glover C J et al: "Mechanical trauma effect on clot structure formation", Thrombosis Research, Tarrytown, NY, US, vol. 10, No. 1, Jan. 1, 1977, pp. 11-25, XP022877328.

Kaibara et al.: "Rheological studies on blood coagulation and network formation of fibrin", Polymer Gels and Networks, Elsevier, Amsterdam, NL, vol. 2, No. 1, Jan. 1, 1994, pp. 1-28, XP024175674 L.

Goto et al., "Characterization of the unique mechanism mediating the shear-dependent binding of soluble von Willebrand factor to platelets", JBC, 1995, 270(40):23352-23361.

Moake et al., "Involvement of large plasma von Willebrand factor (vWF) multimers and unusually large vWF forms derived from endothelial cells in shear stress-induced platelet aggregation", J. Clin. Invest., 1986, 76:1456-1461.

Horn "Addition of a polarizing microscope to the Weissenberg Rheogoniometer", Rev. Sci. Instrum., 1979, 50(5):659-661.

* cited by examiner

*Primary Examiner* — Bin Shen
(74) *Attorney, Agent, or Firm* — Ward and Smith, P.A.

(57) ABSTRACT

A device, system and method is disclosed in which small volume blood samples are subjected to shear forces and shear stresses between two parallel planar surfaces to which linear motion trajectories are imparted. The formation of clots or coagulation of the sample is measured from dynamic mechanical coupling which occurs between the two parallel planar surfaces. Detection of the coagulation response can be achieved through optical probing or by measurement of physical effects of the blood sample binding to the planar surfaces, and restricting movement thereof.

12 Claims, 3 Drawing Sheets

PARALLEL PLATES WITH A SMALL GAP (50-250μm)

SAMPLE ⇒

⇒ $V_1$

⇐ $V_2$

PLATES SLIDE PAST EACH OTHER WITH CONTROLLED VELOCITY.
THIS CREATES A SHEAR STRESS BETWEEN THE PLATES:

$$t = \mu V/d$$

WHERE: $t$ = SHEAR STRESS, $\mu$ = VISCOSITY, $V = V_1 - V_2$, $d$ = GAP BETWEEN PLATES

PORTABLE COAGULATION MONITORING DEVICE FOR ASSESSING COAGULATION RESPONSE

CROSS REFERENCE TO RELATED APPLICATIONS

This application is a divisional of U.S. patent application Ser. No. 12/971,013 filed Dec. 17, 2010, now U.S. Pat. No. 8,450,078 issued May 28, 2013, entitled "Portable Coagulation Monitoring Device and Method of Assessing Coagulation Response", the application of which claims priority to U.S. Provisional Application Ser. No. 61/287,780 filed Dec. 18, 2009, entitled "Portable Coagulation Monitoring Device, System and Method of Use"; the disclosures of which are expressly incorporated by reference herein in their entireties.

FIELD OF THE INVENTION

The invention relates to a device, and method which allows rapid assessment of coagulation response. More particularly, the invention relates to such a device and method which provides extensive and complex information on coagulation response, including platelet function and fibrin polymerization to allow selection of appropriate treatment protocols, in particular for trauma induced coagulopathies but also for the diagnosis of hereditary or acquired abnormalities of coagulation, such as von Willebrand disease or hemophilias.

BACKGROUND OF THE INVENTION

The process by which the body prevents blood loss is referred to as coagulation. Coagulation involves the formation of a blood clot (thrombus) that prevents further blood loss from damaged tissues, blood vessels or organs. This is a complicated process with a cellular system comprised of cells called platelets that circulate in the blood and serve to form a platelet plug over damaged vessels and a second system based upon the actions of multiple proteins (called clotting factors) that act in concert to produce a fibrin clot. These two systems work in concert to form a clot and disorders in either system can yield disorders that cause either too much or too little clotting.

Platelets serve three primary functions: (1) sticking to the injured blood vessel (a phenomenon called platelet adherence), (2) attaching to other platelets to enlarge the forming plug (a phenomenon called platelet aggregation), and (3) providing support for the processes of the coagulation cascade (molecules on the surface of platelets greatly accelerate several key reactions)

When a break in a blood vessel occurs, substances are exposed that normally are not in direct contact with the blood flow. These substances (primarily collagen and attached multimeric von Willibrand factor) allow the platelets to adhere to the broken surface. Once a platelet adheres to the surface, it releases chemicals that attract additional platelets to the damaged area, referred to as platelet aggregation. These two processes are the first responses to stop bleeding. The protein based system (the coagulation cascade) serves to stabilize the plug that has formed and further seal up the wound.

The support role of the platelet to the coagulation cascade is provided, in part, by one of the components on the outside of a platelet, called phospholipids, which are required for many of the reactions in the clotting cascade. The goal of the cascade is to form fibrin, which will form a mesh within the platelet aggregate to stabilize the clot. All of the factors have an inactive and active form. Once activated, the factor will serve to activate the next factor in the sequence until fibrin is formed. The coagulation cascade takes place at the site of a break in a blood vessel that has the platelet aggregate. Fibrin forms a mesh that, in concert with the platelets, plugs the break in the vessel wall. The fibrin mesh is then further stabilized by additional factors which cross-linkup the clot (much like forming an intricate network of reinforced strands of fibrin).

In the case of trauma induced bleeding, it is important to understand very quickly the clotting response of a particular individual in order to apply appropriate therapy to treat bleeding and ensure that the trauma is dealt with appropriately. Defective platelet functions, both primary (adhesive, von Willibrand factor interaction) and secondary (fibrin polymer organization and polymerization, integrin function) are recognized as a particularly important contributor in prolonged non-compressible bleeding. The development of hemostatic disorders in trauma patients, and associated progression in hemorrhagic and other shock states, can be due to different factors and thus require different therapies.

Currently, thromboelastography (TEG) is the accepted clinical standard for testing the efficiency of whole blood coagulation. For purposes of this disclosure, it should be noted that by "whole blood" is meant a mixture of whole blood with one or more substances, a fraction of whole blood containing one or more of the constituents of whole blood, a fraction of whole blood mixed with one or more non-blood substances, or a purified blood constituent, such as blood platelets or serum, a reconstituted blood preparation, a modified blood sample, or a blood substitute.

A TEG system was first developed in Germany in 1948 and has been incrementally improved since then. However, its principle of operation remains the same.

Traditional TEG requires a relatively large sample of blood, i.e., about 0.36 ml in a small cup. A pin is inserted into the blood and is rotated in a sinusoidal oscillation through a small angle at a low frequency. The device measures coupling of motion through rotation over time. It does not measure platelet adhesion, only polymerization of fibrin, and does not allow for mechanical activation of the coagulation response through shear forces. Thus, the information obtained from a TEG analysis falls far short of our current understanding of coagulation response, and requires excessive amounts of time which could result in inappropriate treatment for trauma being applied, leading to adverse results to a patient, possibly even death.

Another device generally known as the PFA-100 attempts to mimic a blood vessel by forcing blood flow through a narrow channel leading to a filter which has an aperture therein. The device measures the time for the aperture to clog and is essentially indicative of platelet function response which results in clogging. The time of closure of the aperture indirectly provides an indication of clotting due to platelet response. The use of such devices as TEG and the PFA-100 requires intensive laboratory training and upkeep, and they are not easily used in the field.

Accordingly, it is desirable to provide a portable coagulation monitoring device for diagnosis of trauma-related coagulopathies in the field, which yields rapid results, including extensive information about the complex mechanisms involved in coagulation, from a small sample of blood. More specifically, it is important to provide such a device which can be used by first responders under conditions encountered in the field, providing real time information, which allows for immediate treatment of a hemorrhaging event, as compared to prior art systems and devices which could result in delays of 45 minutes or more during what is considered an important initial time period for critical care to be applied and which use non-anticoagulated blood samples that do not have to be treated with activators and initiators as surrogates for the true coagulation process.

SUMMARY OF THE INVENTION

In one aspect, the invention relates to a device for measuring coagulation response in a native, non-anticoagulated blood sample. The device includes two members or plates each having surfaces facing each other, and spaced an amount sufficient to allow a relatively small sample of blood to contact both surfaces at the same time without an air space between.

The plates are movable relative to each other in a parallel and linear direction, and the spacing is such that the components of blood can initiate coagulation or adherence to each of the surfaces. A drive mechanism is connected to either one or both of the members for linearly moving one or the other relative to each other when a blood sample is in contact with their surfaces. An optical detection sensor system is provided for detecting interaction of light with a blood sample located between the two members, with the interaction of light and detection thereof providing an indication of coagulation response of the blood sample. More specifically, with appropriate positioning of light source and detectors, over time and in accordance with the variation of the movement of the members to generate a particular shear rate, information about both platelet response, fibrin response and other responses of the blood components during coagulation can be obtained.

More specifically, the device allows for the measurement of coagulation response based on the knowledge that the biophysical response of blood depends in part on the relative shear rate between the blood and surfaces with which it is in contact. More specifically, the higher the shear rate, the greater the platelet response so that the platelets then stick to the surfaces of the plates, and thereby trigger the fibrin polymerization and couple the motion of the two plates when only one is driven by the motors. More specifically, it is recognized that in hemorrhaging events platelets need to react quickly so the use of a high shear rate for a short time period can allow accurate assessment of platelet response for these conditions. Thereafter, lower shear rates can be employed in terms of relative movements of the plates or members with respect to each other, to obtain an accurate assessment of fibrin response, or at an intermediate shear rate, both fibrin and platelet response.

"Shear" here is defined as the acceleration force felt by a particle in the moving bulk flow of fluid (blood) at the interface with the stationary solid (face of the glass plates). The shear "rate" is the differential of velocities felt on different aspects of the particle's cross-sectional area and is dependant on the particle's distance from the stationary surface.

In a preferred aspect, the first member and second members are plates making up a blood sample collection cartridge which is removable from the device. In the case that one or both plates are moved with respect to each other, the device is programmed for moving the plates at different speeds relative to each other for detecting different mechanisms involved in a coagulation response of a blood sample, as previously discussed with respect to shear.

The optical detection system is adapted for detecting binding of the blood sample to the surfaces to couple the motion of the plates relative to each other as an indication of platelet response during coagulation. In addition, the system can also probe fibrin response.

Other features and details of the device are described in the detailed discussion which follows, the Appendices hereto, and in the appended claims in which the invention is described in a nonlimiting manner.

In an alternative aspect there is provided a method of measuring coagulation response in blood sample. A sample droplet of blood is placed between and in contact with facing surfaces of oppositely disposed plates. At least one or both plates are moved linearly with respect to the other at a predetermined rate. The coagulation response of the droplet is optically detected.

To detect two different types of coagulation response, the plates can be moved relative to each other at a first speed and a response optically detected, and thereafter moved at a second speed which is slower than the first speed and a second response optically detected, typically fibrin polymerization. In addition, in the case where only one plate is moved, it should be appreciated that the visco-elastic response of the blood sample on the surfaces of both plates can cause the movement of the first plate to induce movement of the second plate ("coupled motion"), which can be measured as indicative of visco-elastic response of the blood, ultimately leading to conclusions which may be inferred relative to coagulation response. Moreover, by moving the plates at different speeds over time, changes in the visco-elastic state of the blood sample may be measured as a clot is formed, which is also indicative of coagulation response.

Optical detection may be done by transmitting light into the sample droplet, and detecting at least one of transmission, reflection and refraction of the light through the sample droplet at respective light detectors. Analog signals may be generated from the detection representative of coagulation properties of the blood in the sample droplet. The plates are preferably made of glass, more specifically transparent glass, to allow light transmission of 90% or more of the incident light intensity.

These and other advantages and features that characterize the invention are set forth in the claims annexed hereto and forming a further part hereof. However, for a better understanding of the invention, and of the advantages and objectives attained through its use, reference should be made to the Drawings, and to the accompanying descriptive matter, including Appendices I, II, III, and IV which are specifically incorporated in their entirety by reference herein, in which there are described exemplary embodiments of the invention.

DETAILED DESCRIPTION OF THE INVENTION

Figure 1:
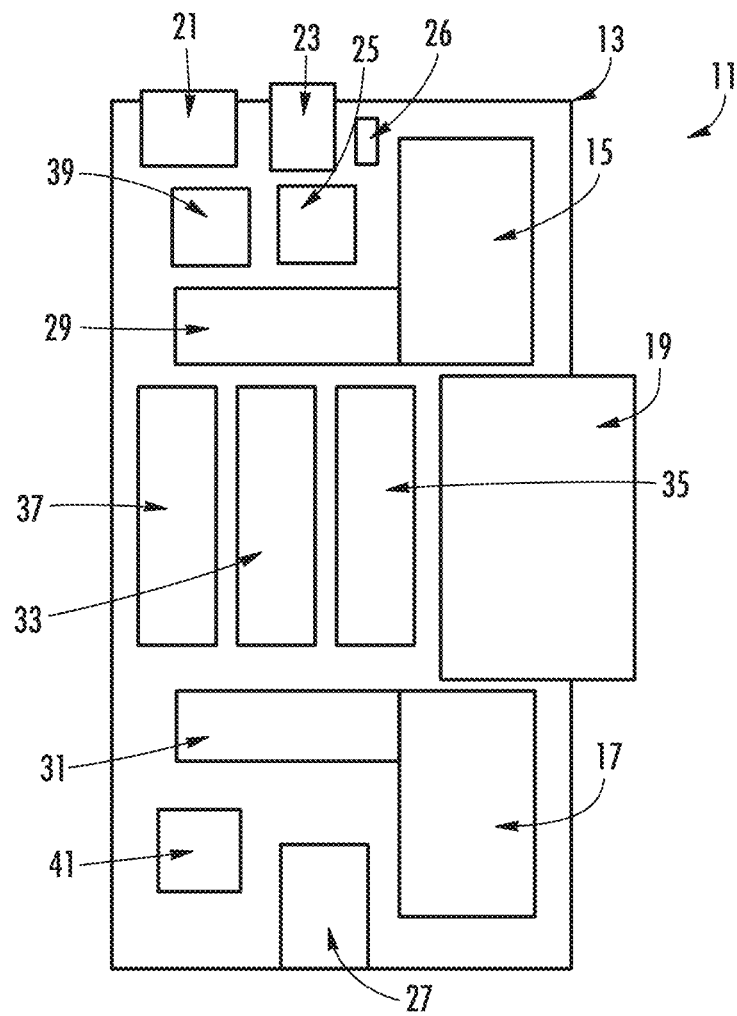
FIG. 1 is a schematic diagram illustrating various components making up the device and system in accordance with the invention.

FIG. 1 illustrates in schematic form an exemplary portable coagulation monitor or assay device 11 for diagnosis of trauma or other related coagulopathies in which it is important to assess coagulation response to optimize treatment, for example, in critical field situations wherein the first hour is critical in terms of preventing long-term debilitating events or even death.

The device is housed in an impact resistant housing 13 which has all the components housed thereon in a conventional manner.

Figure 2:
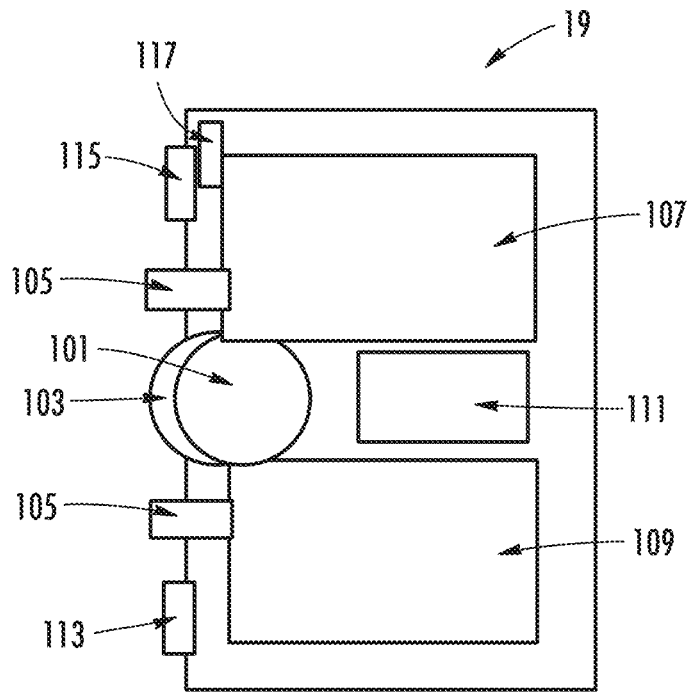
FIG. 2 is a schematic diagram of a sample cassette in which a sample droplet may be loaded, and which may be employed in an exemplary embodiment of the portable coagulation monitor in accordance with the invention, for example, as shown in FIG. 1.

At least one and preferably a pair of linear voice coil actuator motors 15 and 17 are provided for driving movement of sample plates in a removable blood sample cassette which is illustrated in greater detail in FIG. 2. While the motors 15 and 17 and removable blood sample cassette 19 have been described briefly, the remaining components are discussed generally with reference to the drawings in a clockwise manner beginning with the data card port 21 in the upper left-hand corner of the device.

The data card port 21 is useful for receiving an FD card or any memory module, including data on the module for calibrating the device 11, and/or for removing data from the device 11 for input into another system in which the data can be analyzed. A USB port 23 allows for direct interface with a computer, for example, under the control of a physician for a more complex analysis.

Microcontroller 25 operates with EEPROM 26 and handles data from the USB port and the data card port 21 and can provide control for a user interface (not shown) such as an LCD display which provides initially acquired data and analysis thereof to a user using the device. Linear voice coil actuator motors 15 and 17, and the removable blood sample cassette 19 have been briefly described and will be discussed in greater detail hereinafter.

A wireless link 27, such as for transmitting data in the RF or IR spectrum, is also provided, and provides an additional means for communicating data and programming to and from the device. Optical displacement sensors 29 and 31 detect where the linear voice coil actuator motors 15 and 17 are located and control the limits of movement thereof. The digital synthesizer module 33 serves to control operation of the motors 15 and 17 through motor drivers 35 by generating the necessary waveforms to drive the voice coil actuator motors 15 and 17.

The ADC module 37 is an analog to digital converter which obtains data from the optical or physical measurements conducted on a sample in the removable blood cassette 19, converts the data into digital form and supplies it to microcontroller 39 which manages the data obtained to provide useful results to a user of the device.

A 3-axis accelerometer 41 is a conventional device which takes into account outside effects and vibrations on the device 11, and serves to cancel the effects of these vibrations on any data collected as a result of analysis of a sample.

The removable blood sample cassette 19 is shown in FIG. 2 in schematic form and includes an upper sample plate 101 and a lower sample plate 103 between which can be deposited a sample droplet of blood. Linkages 105 to the voice coil actuator motors on the device are provided, which are connected to an upper linear compliant mechanism 107 and a lower linear compliant mechanism 109 which serve to drive movement of the upper and lower plates respectively. Optical sensors 111 are provided in position relative to the sample plates for detecting light being projected from, for example, a laser or other light source (not shown), through and into a sample between the plates. The light can then be detected as light transmitted through the sample, reflected, refracted or otherwise modified in the path through the sample, and detected by optical sensors 111 to obtain information about the coagulation properties of the blood sample.

A power link 113 serves for connection to a power supply such as, for example, batteries or other form of power. A data link 115 can also be provided to allow data collected from the sample and stored on an EEPROM 117 to be downloaded from the device. In this context, it will be appreciated by those of ordinary skill in the art that the data link 115 and EEPROM 117, when the cassette 19 is received in the device 11, can be connected to the various electronic components within the device 11 for having data uploaded and downloaded thereto.

Figure 3:
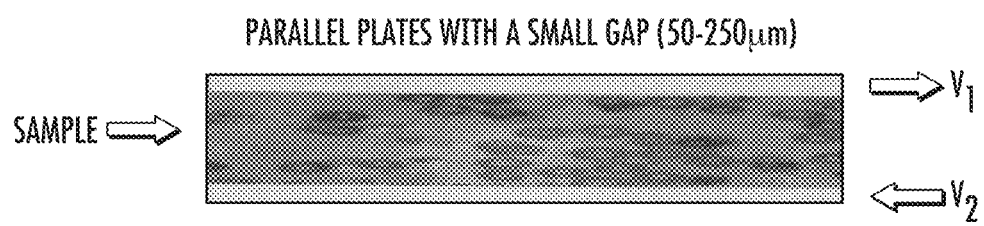
FIG. 3 in a schematic diagram illustrating relative movement of two plates in contact with blood to cause shear and initiate clottING response

As may also be appreciated by those of ordinary skill in the art, FIG. 3 further illustrates the operation of the device in accordance with the invention and with parallel plates, typically having a small gap of about 50 to about 250 µm between the parallel plates. They slide past each other with controlled velocity to create a shear stress between the plates which is represented as $T=\mu V/D$ where T equals shear stress, $\mu$=viscosity, $V=V1+V2$, wherein V is equal to the relative linear velocity of the plates, and D=gap between the plates.

Figure 4:
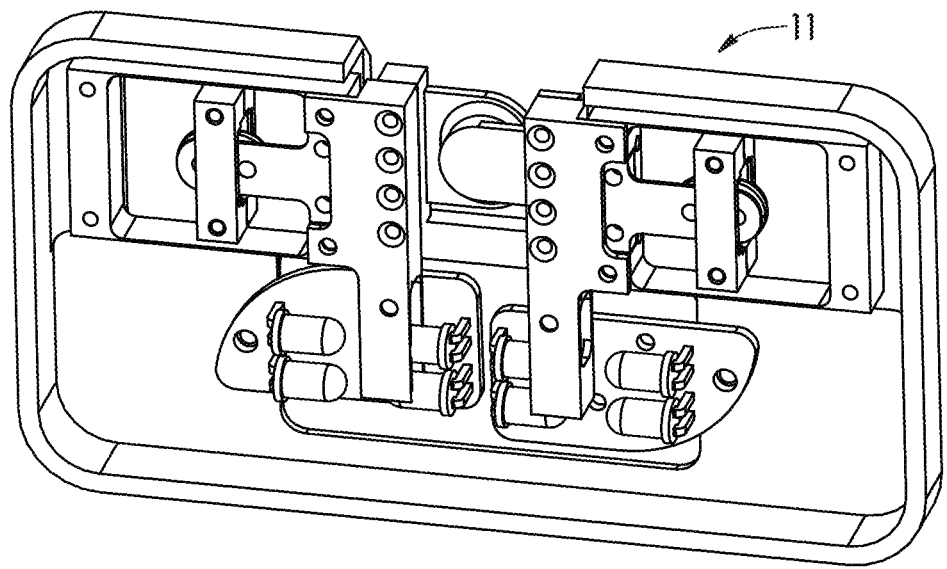
FIG. 4 is a perspective view of an embodiment of the device of the invention.

FIG. 4 further illustrates in assembly view, a device 11 in accordance with the invention showing various components thereof. As may be appreciated from FIG. 4, the device is pocket-sized, preferably with overall dimensions similar to an iPhone, of about 12 cm by about 6 cm by about 2 cm. The device 11 is ruggedized with an internal accelerometer compensating for impacts and vibration. As designed it is versatile and can measure platelet and fibrin clotting over a wide dynamic range of shear. Yet still further, the device 11 can operate on USB hub power as a peripheral device with components which are readily manufactured and assembled. Typically, biophysical resolution is less than about 2µ displacement, and the device 11 allows for a wide range of shear stresses and complete optical access.

Figure 5:
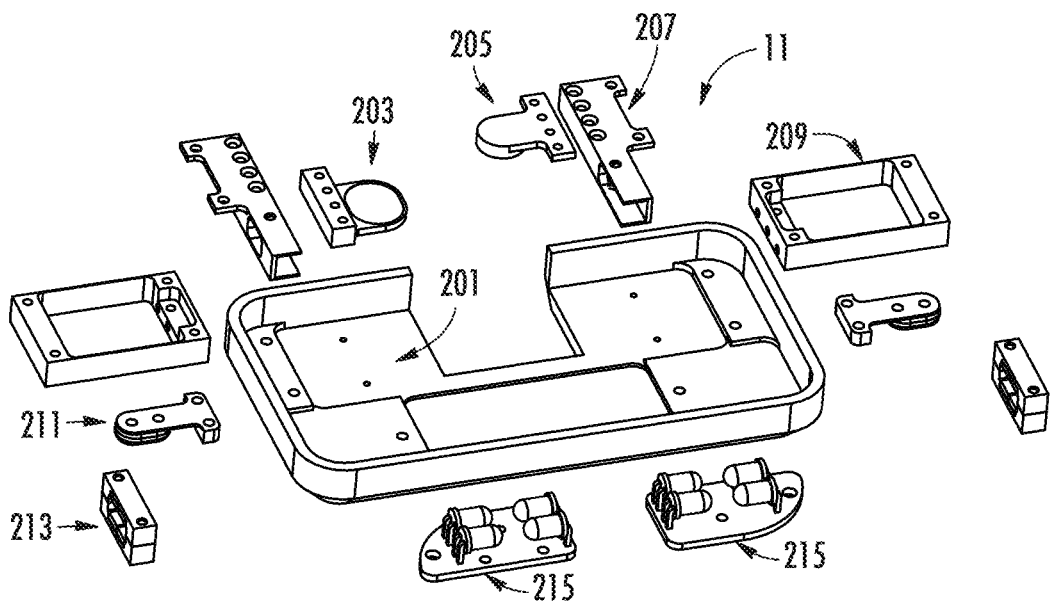
FIG. 5 is an exploded view of an embodiment of the device of the invention.

As further illustrated in the exploded view of FIG. 5, the device 11 preferably is made of a monolithic CNC-machined housing, of materials such as Acetal, 6Al-4V Ti, 2024 Al. A bottom sample window 203 cooperates with a top sample window 205 and they are moved by displacement sensor arms 207. A monolithic compliant four-bar mechanism 209 made typically of aluminum is associated with the displacement sensor arms 207. Motor assemblies 211, typically a VCA motor coil assembly, serves to move the various components and is associated with a magnet assembly 213, typically made of rare earth. Optical sensor arrays 215 serve to interrogate and measure the clotting response. The sensor arrays 215 are typically infra-red differential displacement sensor arrays.

Preferably in the device, the first and second surfaces of the plates 101 and 103 have, at least, been coated with textures, substances or other materials to induce, slow or otherwise modify the coagulation process so as to select for or against specific aspects of coagulation of the sample for diagnostic or other purposes. Modification to the surfaces can include those that enhance platelet or blood protein binding reactivity or activation. Similarly, such modification can reduce platelet or blood protein binding reactivity, or activation as will become more clearly evident from the following detailed discussion of such treatments or coatings.

The device is capable of analyzing blood rheology and coagulation of fresh whole blood or some fraction thereof without the need to add external reagents, such as tissue factor, kaolin, initiator, citrate and others. Such substances and others may electively be added for detailed analytical reasons, but in the most desired embodiment of the device, they are not necessary.

In accordance with the assembly, the device 11, is configured for measuring in real time or with minimal delay the dynamic balance between pro and anti thrombotic hemostatic status by sequential samples from the same person or animal. In a more preferred aspect, the motors 15 and 17 are linear voice coil actuator motors, but can be any other type of device capable of driving linear motion.

In one embodiment, detection of coagulation is done optically by measuring mechanical interaction between the first and second surfaces of the plates 101 and 103 resulting from changes in the viscosity of the sample fluid and binding to the plate surfaces. In a preferred aspect, the relative motions between the two plates 101 and 103 is controlled to generate arbitrarily selected wave forms to induce desired fluid shear rates at selected amplitudes, frequency, duration, and sequence such that the device is enabled to emulate fluid shear as desired over a very broad range, from DC (zero shear) to shear rates that would cause fluid cavitation and subsequent destruction of the cellular components of the sample, and continuously including all points in the shear rate spectrum between these two points.

More specifically, the shear rate is controlled in a sequence of values to generate specific protocols or plate motion paradigms for targeted diagnostic or analytic objectives, such as rapid initiation of primary coagulation, destructive or non-destructive viscoelastic evaluation of early, mid-phase, or late-phase clotting, emulation of clinically accepted or otherwise recognized shear rate protocols for comparison with other commercial or experimental devices, or validation testing against known standards. While light can be used for optical detection it is clear that the full electromagnetic spectrum of waves can be used to generate analog signals representative of coagulation properties of the sample droplet for both primary and secondary coagulation mechanisms.

It should be noted that when the term "blood sample" is used herein, it is intended to mean whole blood, a mixture of whole blood with one or more substances, a fraction of whole blood containing one or more of the constituents of whole blood, a fraction of whole blood mixed with one or more non-blood substances, or a purified blood constituent, such as blood platelets or serum, a reconstituted blood preparation, a modified blood sample, or a blood substitute.

In a specific embodiment, interchangeable sample cassettes 19 can be employed, each one serving a different analytical and maintenance or calibration function. One cassette 19 can be for regular calibration and validation of the device 11. Alternatively, such a disposable and replaceable cassette 19 can serve to calibrate the device 11, receive the blood sample, hold the blood sample, allow different sample chamber geometries for different test protocols, maintain sample viability during a test, serve for safe removal of the sample for storage such a freezing, freeze drying, etc., or for sample disposal without exposure to the blood sample. In one embodiment, the cassette 19 allows for collection of the blood sample by means of simple capillary action eliminating the need to use sample extraction and metering devices.

As will be appreciated by those of ordinary skill in the art, the cassettes 19 may be manufactured for different tests and applications with different sample plate spacings, different surface chemical and optical properties, and similar variations for analysis and validation testing.

The cassette 19 may contain optical interrogation electronics allowing detection of blood status, type, pH, oxygenation, metabolites, toxins, or other measures detectable by optical means. The device 11 is such that through its electronics it can be interfaced with other laboratory systems such as microscopes, etc. The plates 101 and 103 are preferably optically clear to allow optical signals to pass through the blood sample allowing direct optical visualization of a portion or all of the blood sample between the planar surfaces. This allows transmission, reflection, internal reflection, selective absorption, polarization or optical rotation, frustrated internal reflection (either partial or total), and conduction of laser beams or other light surfaces.

As already noted, the cassette 19 may contain a non-volatile permanent memory storage device such as EEPROM 117, for containing initial data that identifies the cassette, lot, manufacture date, and details of construction, as well as allowing for storage of key data such as user-defined sample identification information, test initiation time, test duration, and specified test output data and results, to be permanently stored with each sample until destroyed.

The cassettes 19 may contain additional fluids or other materials such as additives, preservatives, sealing or barrier agents, and other like agents which can be added to or layered on top of the blood sample before, during, or after testing. In one embodiment not specifically shown in the drawings, instead of linear motion, rotary motion can be used to induce shear in addition to or as a replacement for linear displacement previously discussed.

As constructed, the device 11 is capable of delivering mechanical shear to the blood sample over a wide dynamic range of mechanical oscillations, including 0.0001 Hz to 1000 Hz employing a digital synthesizer 33 previously disclosed, typically a dual channel synthesizer, with the ability to generate regular periodic waveforms such as sine waves, triangle waves, square waves of varying duty cycle, frequency, and amplitude, plus the ability to generate arbitrary waveforms with rapid changes in all parameters, such as slew rate, amplitude, etc., or which may also hold steady (DC) mechanical displacements of either one or both of the planar surfaces. The motors 15 and 17 may be driven by drivers 35 in a manner where either one or both drive mechanisms are coupled with the motors 15 and 17, and can be employed simultaneously to effect linear motion, or where either may be employed as a single or in concert with the other mechanism serving as a precision sensor for mechanical displacement. In such a system, mechanical features are incorporated such as 4-bar of multi-bar monolithic compliant mechanisms, to eliminate mechanical hysteresis from the use of sliding or rolling bearing surfaces other than those associated with the blood sample itself.

Data analysis and reduction software may be incorporated into the device electronics to allow the resulting measured parameters of blood coagulation to be stored for later retrieval, transferred to a computer or other device for display, storage, or analysis, displayed graphically, displayed in numerical form with physical units, or displayed in icon or symbolic form to indicate a specific diagnosis, clinical indication, or parametric change of clinical significance. The software will allow the resulting data to be represented in such a way to allow the user to compare the results directly with similar or analogous results that would be expected from other devices with similar functions, or to display the data in such a way to render comparison with accepted standard values or ranges for coagulation parameters. In this context, it is noted that a user interface (not shown) is implemented with the device such as a LCD user interface.

The device 11 employs plates 101 and 103 motion protocols coupled with data analysis and data reduction software to enable the direct assessment of, for example, platelet function, function of the coagulation cascade, red blood cell (RBC) rheology, RBC aggregation, the effects of pro- or anti-coagulation agents, fibrinolysis, and other characteristics of blood coagulation. The device 11, with appropriate user requirements and user interfaces may be classified as "simple" (CLIA "waived" classification) to permit use in-home and by unskilled users. The disposable cassette is configured for collecting and holding the blood sample through simple unskilled collection of the fluid sample without requiring the use of any measuring pipette, syringe, or other metering device for blood sample collection. The cassette 19 allows safe handling, storage, retrieval, and disposal of the collected blood sample and may be manufactured to allow adjustment of the surface area and spacing between the plates to allow the use of very small volumes of blood, typically on the order of less than about 1 mL.

The device 11 and cassette 19 allows optical microscopic inspection of most or all of the sample volume before, during, or after coagulometric analysis, using both standard and inverted microscopic arrangements. The device 11 can be employed to diagnose and quantify diseases and derangements of blood coagulation, including but not limited to induced, acquired, and congenital conditions such as trauma-induced coagulopathies (TIC), von Willebrand Disease (vWD), coagulation factor consumption, platelet consumption, thrombasthenia, platelet metabolic exhaustion, hemodilution, over-activation of protein C, S, and fibrinolytic pathways, altered RBC rheology, and improperly administered coagulation modulating therapeutics, and other diseases and conditions of blood coagulation.

Yet still further, the device 11 can rapidly assess coagulopathies in the field in a period of time less than 15 minutes, and preferably less than 4 minutes, at the site of an injury or trauma, during transport, or at any other time during the course of rescue, first response, treatment, surgical intervention, or recovery. Use of feedback and feed-forward technology serves to stabilize the blood sample to resist the effects of external mechanical noise, vibration, and shock from impact. Testing the time course of changes in both primary and secondary coagulation during the early phase of medical response to trauma and blood loss can be effected. Similarly, intra-surgical testing of primary and secondary coagulation, and changes to these mechanisms during the course of surgery can be accomplished.

The device 11 can be used for rapid in-vitro screening of bioactive compounds intended to affect the mechanisms of primary or secondary coagulation. It can also be used for guidance of clinical treatment of diseases of the mechanisms of primary or secondary coagulation.

Similarly, the device 11 and cassette 19 may be modified for use in the measurement of the rheological properties of other bodily substances of clinical and research interest, such as pulmonary mucous, for the study of and clinical guidance of the treatment of cystic fibrosis, for example, such applications requiring a specially-designed cassette (disposable) and specialized test protocols and firmware, or for use in the study of new and novel fluids with variable rheology.

The device 11 employs opto-electronic and wireless means to allow more than one device to be employed simultaneously, or with multiple samples, each with different test initiation times and different test durations or different sample chamber test protocols, to provide a rich set of coagulation data to a central computer or data collection and display device. This allows that many samples can be monitored simultaneously to track dynamic changes in the coagulation status of blood from an individual during surgery or recovery, or during transport or treatment in the field.

As previously discussed, certain embodiments of the invention may take the form of adding coatings to the plates 101 and 105, typically glass plates, on the surfaces that come into contact with the blood sample. These coatings may be of a character to promote platelet adherence and activation, such as collagen, more specifically type IV collagen, of human or bovine origin. Likewise, the coating may be derived from the extracellular matrix (ECM) of cultured fibroblasts, or from cultured endothelium, or derived from the natural subendothelial tissue of living blood vessels of human or animal origin. Particular molecular components of the matrix, such as vitronectin or fibronectin may comprise the coating or be an enriched feature of the matrix to enhance the adhesion properties. The coating may also be of a synthetic nature to promote platelet adherence and/or activation, such as polyamides or polyglucosamines, more specifically β-N-acetyl polyglucosamine of natural or synthetic origin. Other embodiments may incorporate coatings on the plates 101 and 105 to modulate platelet function, such as materials capable of releasing activators of platelet function, e.g., adenosine diphosphate or epinephrine, or inhibitors of platelet function such as prostaglandins, e.g., prostacyclin or prostaglandin E-1.

Another embodiment of the invention may take the form of adding coatings to the plates 101 and 105 that promote, initiate, or modulate the process of coagulation and fibrin polymerization. These coatings may take the form of materials capable of releasing micronized silica, or kaolin, or tissue factor (natural or recombinant), or other such agents which are known to promote steps in the coagulation cascade. The coatings may also be of a nature to reverse anticoagulants that may be present in the blood sample, such as a material capable of releasing the enzyme heparinase to remove heparin, or mineralized calcium to reverse citrate. These coatings may be preferred for testing of blood from patients that do not have sufficient platelet count or function to be able to initiate coagulation by the shear-induced mechanism of platelet activation. For the same reason, the coatings may incorporate a source of phospholipids, either of natural or synthetic origin, or contain partial or whole thromboplastins to mimic the agents used in standard clinical coagulation tests such as the prothrombin time (PT) or partial thromboplastin time (PTT).

In yet another embodiment of the invention, coatings may be added to the plates that inhibit or modulate or reverse the effects of hyperfibrinolysis in the blood sample, such as materials capable of releasing epsilon amino caproic acid (EACA), or trans-examic acid, or aprotinin, or other antiplasmin compounds or chemicals that affect the action of the enzyme plasmin. These coatings may be preferred for testing of blood from patients in a severe state of hyperfibrinolysis that obfuscates the ability to extract other useful information on the coagulation/hemostasis system components in the sample (and thus the patient) unless the immediate effects of plasmin in the test system are ablated. Likewise, the coatings may contain buffering compounds of acidic or basic nature to adjust the blood sample pH to the optimal desired level of between pH 7.2 to 7.4 or other specified level to avoid loss of information when the sample is overly acidotic or basic due to severe conditions in the patient. These buffering compounds may take the form of released salts or amino acids or other zwitterionic polymeric soluble compounds biocompatible with blood for the purpose of producing and maintaining the desired pH.

These and other coatings to be added to the plates 101 and 105 of the instant invention generally do not alter the geometry of the blood sample space between the plates 101 and 105, or the motion and control of the plates 101 and 105 by the motorized mechanism, beyond the capacity of the system to be adjusted to maintain the required gap within specifications. For that reason, the preferred methods of manufacturing these coatings on the glass plates may include use of electrostatic charging and deposition of the desired materials directly in contact with the glass members, or by layering of thin molecular hydrogels and carrier emulsions containing the desired agents in a releasable form suitable for activation immediately when contacted by the blood sample.

The specified coatings may be comprised of single agents for a singular purpose, or may be a combination mixture of several or more of the specified coatings for multiple supporting purposes. One embodiment may be comprised of having different coatings on the two surfaces, one of one type and the other of a different type or at different density or modification of the similar coating on the opposing member. In a further embodiment one or more coatings may be applied at differing densities or concentration in differing areas of one or both surfaces, or with linear, radial, or other gradients of density of coating on one or both surfaces. The pattern or gradient for each coating type may differ from that of other surface coating treatments on the same or opposing surfaces. While in one exemplary embodiment the surfaces are glass, they may be of any other material capable of accepting the coatings thereon, and of functioning in the manner intended, as will be evident to those of ordinary skill.

While the present invention has been illustrated by a description of various embodiments and while these embodiments have been described in considerable detail, it is not the intention of the Applicants to restrict, or in any way limit the scope of the appended claims to such detail. The invention in its broader aspects is therefore not limited to the specific details, representative devices and methods, and illustrative example shown and described. Accordingly, departures may be made from such details without departing from the spirit or scope of the Applicants' general inventive concept of monitoring global hemostasis function in a portable device employing shear-induced activation of platelets and the full spectrum of response of blood coagulation.

What is claimed is:

1. A device for measuring coagulation response in a blood sample, comprising:
    a first member having a first surface, and a second member having a second surface, said first member positioned for having said first surface facing said second surface of said second member with sufficient space to allow a sample droplet of blood to contact said first surface and said second surface and initiate coagulation, and said first member and second member being linearly movable relative to each other;
    a drive mechanism connected to at least one of said first member and said second member for linearly moving said first member and said second member relative to each other in parallel when a blood sample is in contact with said first surface and said second surface, wherein the drive mechanism comprises at least one motor; and
    an optical detection sensor system for detecting interaction of light with a blood sample located between said first member and second member, as an indication of coagulation response of said blood sample;
    wherein the device further comprises at least one microcontroller for controlling operation of said drive mechanism and optical detection sensor system.

2. The device of claim 1, wherein said first member and second member make up a blood sample collection cartridge which is removable from said device.

3. The device of claim 2, wherein said blood sample collection cartridge further comprises a memory device on said cartridge for storing data relating to a blood sample tested.

4. The device of claim 1, wherein the drive mechanism is programmed for moving the first member and second member at different speeds relative to each other for detecting different mechanisms involved in a coagulation response of a blood sample.

5. The device of claim 1, wherein said optical detector sensor system is adapted for detecting binding of the blood sample to the first surface and the second surface as an indication of platelet response during coagulation.

6. The device of claim 1 wherein the said first and second surfaces (1 and 2) have at least one been treated to induce, slow, or modify the coagulation process for selecting in favor of or against specific aspects of coagulation of the sample for diagnostic or for other purposes.

7. The device of claim 6, wherein said treatment of the surfaces enhances platelet or blood protein binding, reactivity, or activation.

8. The device of claim 6, wherein said treatment of the surfaces reduces platelet or blood protein binding, reactivity, or activation.

9. The device of claim 1, further comprising at least one displacement sensor for detecting and controlling the amount of relative movement between said first member and said second member.

10. The device of claim 1, further comprising a connection interface module for connecting and communicating between the device and an external system.

11. The device of claim 1, wherein said drive mechanism comprises a device capable of driving linear motion.

12. The device of claim 1, further comprising an analog to digital converter connected to optical detection sensor system for converting analog signals indicative of coagulation response of a blood sample into digital signals for storage thereof.

* * * * *